United States Patent [19]
Podolsky

[11] Patent Number: 6,063,755
[45] Date of Patent: May 16, 2000

[54] INTESTINAL TREFOIL PROTEINS

[75] Inventor: Daniel K. Podolsky, Wellesley Hills, Mass.

[73] Assignee: The General Hospital Corporation, Charlestown, Mass.

[21] Appl. No.: 08/476,705

[22] Filed: Jun. 7, 1995

Related U.S. Application Data

[62] Division of application No. 08/191,352, Feb. 2, 1994, abandoned, which is a continuation of application No. 08/037,741, Mar. 25, 1993, abandoned, which is a continuation of application No. 07/837,192, Feb. 13, 1992, abandoned, which is a continuation-in-part of application No. 07/655,965, Feb. 14, 1991, abandoned.

[51] Int. Cl.$^7$ ............................. A01N 37/18; A61K 38/00
[52] U.S. Cl. ............................... 514/2; 530/300; 530/324; 530/350
[58] Field of Search ..................................... 530/350, 300, 530/324; 514/2, 12; 520/388.1, 388.2; 435/7.21; 436/501, 503

[56] References Cited

PUBLICATIONS

Suemori et al., "Identification and characterization of rat intestinal trefoil factor: Tissue– and cell–specific . . . ", *Proc. Natl. Acad. Sci.*, 88:11017–11021 (1991).
Parson, J.A. (Editor) "Peptide Hormones", published by University Park Press see Chapter 1, pp 1–7 by Rudinger, Jun. 1976.
Lazar et al. Mol. Cell. Biology 8(3):1247–52, Mar. 1988.
Burgess et al. J. Cell Biol. 111:2129–38, Nov. 1990.
Babyatsky, M.W. et al. Gastroenterology, vol. 106, No. 4, p. A43 (abstract), Apr. 1994.
Maniatis, T., et al. 1982, Molecular Cloning, A Laboratory Manual, Cold Spring Harbor Laboratory, Cold Spring Habor, New York, pp. 224–246, 270–307, 310–352, 404–433.

Jorgensen, K.D., et al., 1982, Pancreatic Spasmolytic Polypeptide (PSP): III. Pharmacology of a new porcine pancreatic polypeptide with spasmolytic and gastric acid secretion inhibitory effects, Reg.Pep. 3:231–243.

Thim, L., et al., 1982, Pancreatic Spasmolytic Polypeptide (PSP): II. Radioimmunological determination of PSP in porcine tissues, plasma and pancreatic juice, Regulatory Peptides, 3:221–230.

Jorgensen, K.H., et al., 1982, Pancreatic Spasmolytic Polypeptide (PSP): I. Preparation and initial chemical characterization of a new polypeptide from porcine pancreas, Regulatory Peptides, 3:207–219.

Jakowlew, S.B., et al., 1984, Sequence of the pS2 mRNA induced by estrogen in the human breast cancer cell line MCF–7, 12:2861–2878.

Frandsen, E.K., et al., 1986, Receptor binding of pancreatic spasmolytic polypeptide (PSP) in rat intestinal mucosal cell membranes inhibits the adenylate cyclase activity, Regulatory Peptides, 16:291–297.

Rio, M.C., et al., 1988, Breast Cancer–Associated pS2 Protein: Synthesis and Secretion by Normal Stomach Mucosa, Science, 241:705–708.

Podolsky, D.K., et al., 1988, Latent Transformed Growth–inhibiting Factor in Human Malignant Effusions, Cancer Research, 48:418–424.

*Primary Examiner*—Patricia A. Duffy
*Attorney, Agent, or Firm*—Fish & Richardson P.C.

[57] ABSTRACT

Intestinal trefoil factors and nucleic acids encoding intestinal trefoil factors are disclosed. The intestinal trefoil factors disclosed are resistent to destruction in the digestive tract and can be used for the treatment of peptic ulcer diseases, inflammatory bowel diseases and other insults.

8 Claims, 7 Drawing Sheets

```
gaagtttgcg tgctgcc                                                              17
atg gag acc aga gcc ttc tgg ata acc ctg ctg gtc ctg gtt                         62
gct ggg tcc tcc tgc aaa gcc cag gaa ttt gtt ggc cta tct cca                    107
agc caa tgt atg gcg cca aca aat gtc agg gtg gac tgt aac tac                    152
ccc act gtc aca tca gag cag tgt aac aac cgt ggt tgc tgt ttt                    197
gac tcc agc atc cca aat gtg ccc tgg tgc ttc aaa cct ctg caa                    242
gag aca gaa tgt aca ttt                                                        260
tgaagctgtc caggctccag gaagggagct ccacaccctg gactcttgct                         310
gatggtagtg gcccaggta acactcaccc ctgatctgct ccctcgcgcc                          360
ggccaatata ggagctggga gtccagaaga ataaagacct tacagtcagc                         410
acaaggctgt tctaattgcg g                                                        431
```

FIG. 1

Met Glu Thr Arg Ala Phe Trp Ile Thr Leu Leu Val Leu Val
                 5                  10              15
Ala Gly Ser Ser Cys Lys Ala Gln Glu Phe Val Gly Leu Ser Pro
                 20                 25              30
Ser Gln Cys Met Ala Pro Thr Asn Val Arg Val Asp Cys Asn Tyr
                 35                 40              45
Pro Thr Val Thr Ser Glu Gln Cys Asn Asn Arg Gly Cys Cys Phe
                 50                 55              60
Asp Ser Ser Ile Pro Asn Val Pro Trp Cys Phe Lys Pro Leu Gln
                 65                 70              75
Glu Thr Glu Cys Thr Phe
                 80

FIG. 2

```
rITF  METRAFWITLLVLVAGSSCKAQEFVGLSPSQCMAPTNVRVDCNYPTVTSEQCNNRGCC
                                    ::            :: ::   :::
pS2   --------------------------EAQ------TETCTVAPRERQNCGFPGVTPSQCANKGCC
                                                  :: ::::::   ::   :::
PSP   --------------------------EKPAACRCSRQDPKN-RVNCGFPGITSDQCFTSGCC rITF  FDSSIPNVPWCFK------PLQ------ETECT------F
      ::  :: :::::       ::        ::        
pS2   FDDTVRGVPWCFY------PNTIDVPPEECE------F
       : :::::::::       ::        ::
PSP   FDSQVPGVPWCFK------PLP------AQESEECVMEV
```

```
1    gatgctggggctggtcctgcttgtcctccagctctgctgaggagtacgtggggcct      60
     ---+---------+---------+---------+---------+---------+
     M  L  G  L  V  L  A  L  L  S  S  S  A  E  E  Y  V  G  L 61   gtctgcaaaccagtgtgccgtgccggccaaggacagggtgactgcggctaccccatgt    120
     ---+---------+---------+---------+---------+---------+
     S  A  N  Q  C  A  V  P  A  K  D  R  V  D  C  G  Y  P  H  V 121  caccccaaggagtgcaacaaccggggctgctgtttgactccaggatccctggagtgcc   180
     ---+---------+---------+---------+---------+---------+
     T  P  K  E  C  N  N  R  G  C  C  F  D  S  R  I  P  G  V  P 181  ttggtgttcaagcccctgactaggaagacagaatgcacctctgaggcacctccagctg   240
     ---+---------+---------+---------+---------+---------+
     W  C  F  K  P  L  T  R  K  T  E  C  T  F  *

241  cccctgggatgcaggctgagcaccctgcccggctgtgattgctgccaggcactgttcat   300
     ---+---------+---------+---------+---------+---------+

301  ctcagttttctgtcccttgctcccggcaagctttctgctgaaagttcatatctggagc   360
     ---+---------+---------+---------+---------+---------+

361  ctgatgtcttaacgaataaaggtcccatgctccacccgAAAAA                   403
     ---+---------+---------+---------+
```

FIG. 6

INTESTINAL TREFOIL PROTEINS

This is a divisional of application Ser. No. 08/191,352, filed Feb. 2, 1994, now abandoned which is a continuation of application Ser. No. 08/037,741, filed Mar. 25, 1993, now abandoned which is a continuation of application Ser. No. 07/837,192, filed Feb. 13, 1992, now abandoned which is a continuation-in-part of application Ser. No. 07/655,965, filed Feb. 14, 1991, now abandoned.

BACKGROUND

This application is a continuation-in-part of Podolsky, U.S. Ser. No. 07/655/965, filed Feb. 14, 1991.

The field of the invention is peptides useful for treatment of disorders of the digestive system.

Jørgensen et al. (Regulatory Peptides 3:231, 1982) describe a porcine pancreatic peptide, pancreatic spasmolytic peptide (PSP). PSP was found to inhibit "gastrointestinal motility and gastric acid secretion in laboratory animal after parenteral as well as oral administration." It was suggested that "if the results in animal experiments can be confirmed in man, PSP may posses a potential utility in treatment of gastroduodenal ulcer diseases.

SUMMARY OF THE INVENTION

In a first aspect, the invention features a purified nucleic acid encoding an intestinal trefoil factor (ITF).

In preferred embodiments, the intestinal trefoil factor is mammalian intestinal trefoil factor, preferably human, rat, bovine, or porcine intestinal trefoil factor. In another preferred embodiment, the purified nucleic acid encoding an intestinal trefoil factor is present within a vector.

In a related aspect, the invention features a cell that includes a vector encoding an intestinal trefoil factor.

In another related aspect, the invention features a substantially pure intestinal trefoil factor. In a preferred embodiment, the polypeptide is detectably labelled. In a related aspect, the invention features a therapeutic composition that includes an intestinal trefoil factor and a pharmacologically acceptable carrier.

In another aspect, the invention features a monoclonal antibody which preferentially binds (i.e., forms an immune complex with) an intestinal trefoil factor. In a preferred embodiment, the monoclonal antibody is detectably labelled.

In a related aspect, the invention features a method for detecting human intestinal trefoil factor in a human patient. The method includes the steps of contacting a biological sample obtained from the patient with a monoclonal antibody which preferentially binds intestinal trefoil factor, and detecting immune complexes formed with the monoclonal antibody. In preferred embodiments the biological sample is an intestinal mucosal scraping, or serum.

In a related aspect, the invention features a method for treating digestive disorders in a human patient, which method involves administering to the patient a therapeutic composition that includes an intestinal trefoil factor and a pharmacologically acceptable carrier.

In another aspect, the invention features a method for detecting binding sites for intestinal trefoil factor in a patient. The method involves contacting a biological sample obtained from the patient with the factor, and detecting the factor bound to the biological sample as an indication of the presence of the binding sites in the sample. By "binding sites", as used herein, is meant any antibody or receptor that binds to an intestinal trefoil factor protein, factor, or analog. The detection or quantitation of binding sites may be useful in reflecting abnormalities of the gastrointestinal tract.

In another aspect, the invention features substantially pure trefoil factor. In preferred embodiments, the intestinal trefoil factor is human, porcine, or bovine trefoil factor.

The term "intestinal trefoil factor" ("ITF") includes any protein which is substantially homologous to rat intestinal trefoil factor (FIG. 2, SEQ ID NO 2) and which is expressed in the large intestine, small intestine, or colon to a greater extent than it is expressed in tissues other than the small intestine, large intestine, or colon. Also included are: allelic variations; natural mutants; induced mutants; proteins encoded by DNA that hybridizes under high or low stringency conditions to ITF encoding nucleic acids retrieved from naturally occurring material; and polypeptides or proteins retrieved by antisera to ITF, especially by antisera to the active site or binding domain of ITF. The term also includes other chimeric polypeptides that include an ITF.

The term ITF also includes analogs of naturally occurring ITF polypeptides. Analogs can differ from naturally occurring ITF by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring ITF sequence. The length of comparison sequences will generally be at least about 8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occuring ITF by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), *Molecular Cloning: A Laboratory Manual* (2d ed.), CSH Press, hereby incorporated by reference. Also included are analogs that include residues other than naturally occurring L-amino acids, e.g., D-amino acids or non-naturally occurring or synthetic amino acids, e.g., β or γ amino acids.

In addition to substantially full-length polypeptides, the term ITF, as used herein, includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of ITF can be generated by methods known to those skilled in the art. The ability of a candidate fragment to exhibit a biological activity of ITF can be assessed by methods known to those skilled in the art. Also included in the term are biologically active ITF polypeptides containing amino acids that are normally removed during protein processing, including additional amino acids that are not required for the biological activity of the polypeptide, or including additional amino acids that result from alternative mRNA splicing or alternative protein processing events.

An ITF polypeptide, fragment, or analog is biologically active if it exhibits a biological activity of a naturally occurring ITF, e.g., the ability to alter gastrointestinal motility in a mammal.

The invention also includes nucleic acid sequences, and purified preparations thereof, that encode the ITF polypeptides described herein. The invention also includes antibodies, preferably monoclonal antibodies, that bind specifically to ITF polypeptides.

As used herein, the term "substantially pure" describes a compound, e.g., a nucleic acid, a protein, or a polypeptide, e.g., an ITF protein or polypeptide, that is substantially free from the components that naturally accompany it. Typically, a compound is substantially pure when at least 60%, more preferrably at least 75%, more preferably at least 90%, and most preferrably at least 99%, of the total material (by volume, by wet or dry weight, or by mole per cent or mole fraction) in a sample is the compound of interest. Purity can be measured by any appropriate method, e.g., in the case of polypeptides by column chromatography, polyacrylamide gel electrophoresis, or HPLC analysis.

By "isolated DNA" is meant that the given DNA is free of the genes which, in the naturally-occurring genome of the organism from which the given DNA of the invention is derived, flank the given DNA. The term "isolated DNA" thus encompasses, for example, cDNA, cloned genomic DNA, and synthetic DNA. A "purified nucleic acid", as used herein, refers to a nucleic acid sequence that is substantially free of other macromolecules (e.g., other nucleic acids and proteins) with which it naturally occurs within a cell. In preferred embodiments, less than 40% (and more preferably less than 25%) of the purified nucleic acid preparation consists of such other macromolecules.

"Homologous", as used herein, refers to the subunit sequence similarity between two polymeric molecules, e.g., between two nucleic acid molecules, e.g., two DNA molecules, or two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half, e.g., 5 of 10, of the positions in two compound sequences are homologous then the two sequences are 50% homologous, if 90% of the positions, e.g., 9 of 10, are matched or homologous the two sequences share 90% homology. By way of example, the DNA sequences 3'ATTGCC'5 and 3'TATGGC'5 share 50% homology. By "substantially homologous" is meant largely but not wholly homologous.

The ITF proteins of the invention are resistant to destruction in the digestive tract, and can be used for treatment of peptic ulcer diseases, inflammatory bowel diseases, and for protection of the intestinal tract from injury caused by bacterial infection, radiation injury or other insults. An ITF protein, fragment, or analog can also be used to treat neoplastic cancer.

Other features and advantages of the invention will be apparent from the following description of the preferred embodiments thereof, and from the claims.

DETAILED DESCRIPTION

The drawings will first be briefly described.

Purification and Cloning of rITF

An inhibitor of soft agar colony formation by human breast carcinoma-derived BT-20 cells (ATTC HTB79) was isolated from cytology-positive human malignant effusions (Podolsky et al., Cancer Res. 48:418, 1988; hereby incorporated by reference). The factor also inhibited soft agar colony formation by human colon carcinoma-derived HCT-15 cells (ATTC-CCL225). Inhibition was not observed for polyoma and murine sarcoma virus transformed rodent fibroblast lines. The isolated factor (transformed cell-growth inhibiting factor or TGIF) had an apparent molecular weight of 110,000 kD and appeared to consist of two 55,000 kD subunits linked by sulfhydryl bonds.

The purified protein was partially sequenced. The sequence from the amino terminal 14 amino acids was used to produce a set of degenerate oligonucleotide probes for screening of a rat intestinal epithelial cell cDNA library.

Figure 1:
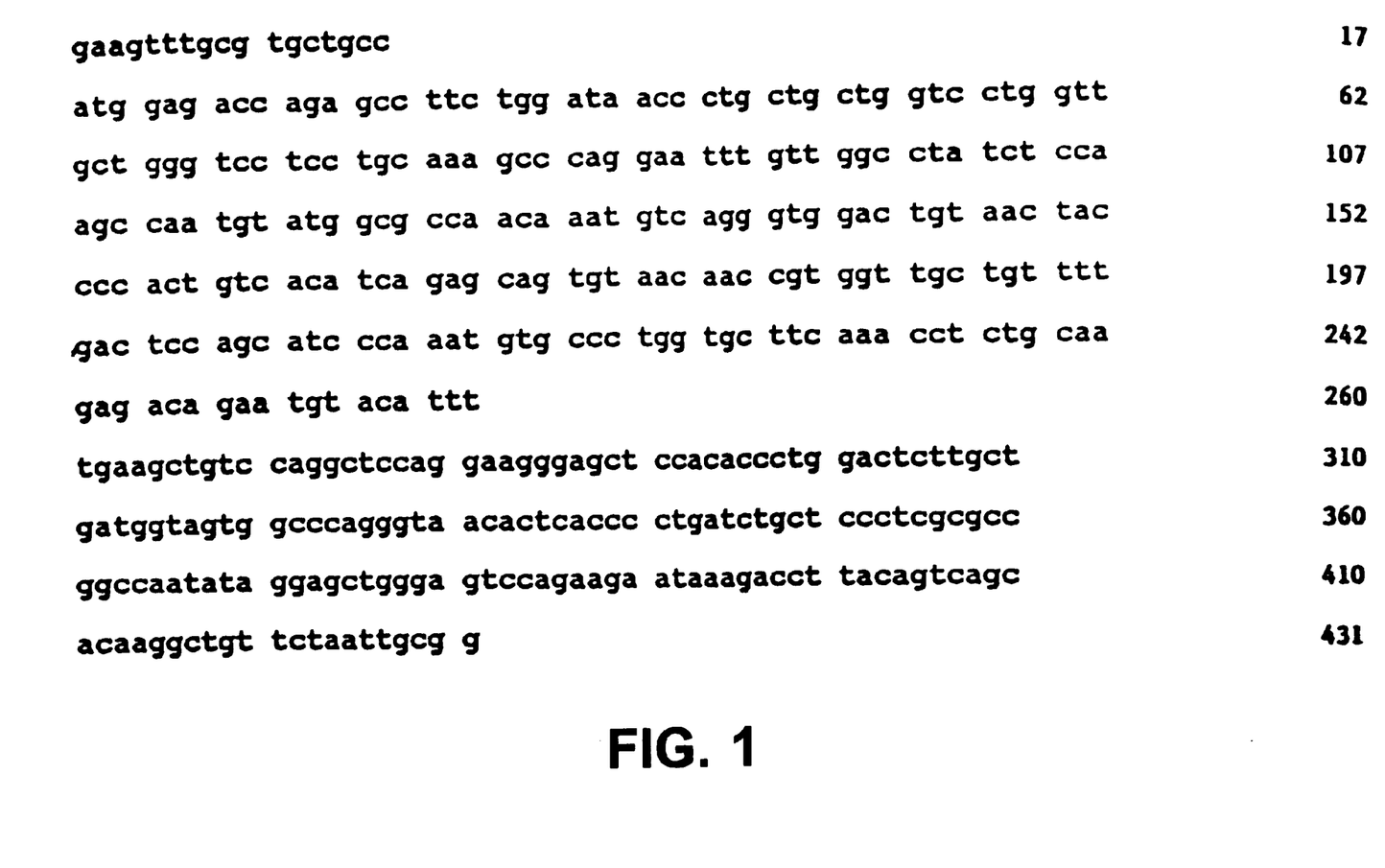
FIG. 1 is a depiction of the nucleotide sequence of rat intestinal trefoil factor (SEQ ID NO: 1).

A rat intestinal cDNA library (Lambda ZAP® II, Stratagene, La Jolla, Calif.) was produced by standard techniques (Ausubel et al., eds., Current *Protocols in Molecular Biology,* John Wiley & Sons, New York, 1989) using cells purified by the method of Weisner (*J. Biol Chem.* 248:2536, 1973). Screening of the cDNA library with the fully degenerate oligonucleotide probe described above resulted in the selection of 21 clones. One of the clones (T3411) included a core sequence which encoded a single open reading frame. The nucleotide sequence of the open reading frame and flanking DNA is presented in FIG. 1 (SEQ ID NO 1). The insert present in T3411 was nick translated (Ausubel et al., supra) to produce a radioactively labelled probe for Northern blot analysis of rat poly(A)$^+$ RNA. Northern analysis demonstrated that RNA corresponding to the cloned cDNA fragment was expressed in small intestine, large intestine, and kidney; no expression was detected in the lung, spleen, heart, testes, muscle, stomach, pancreas, or liver. In the tissues in which the RNA was expressed, the level was comparable to that of actin.

Figure 2:
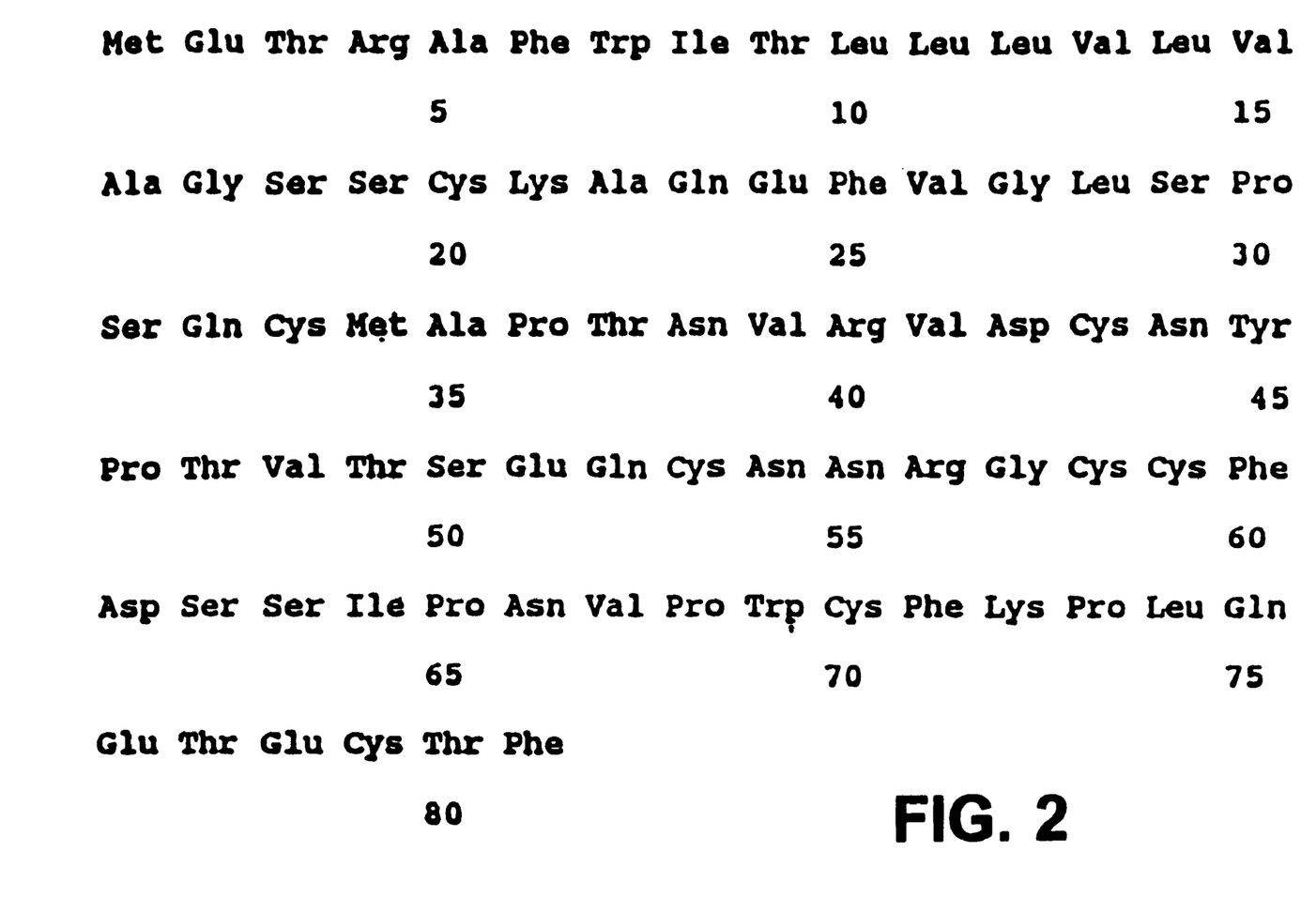
FIG. 2 is a depiction of the deduced amino acid sequence of rat intestinal trefoil factor (SEQ ID NO: 2).
Figure 3:
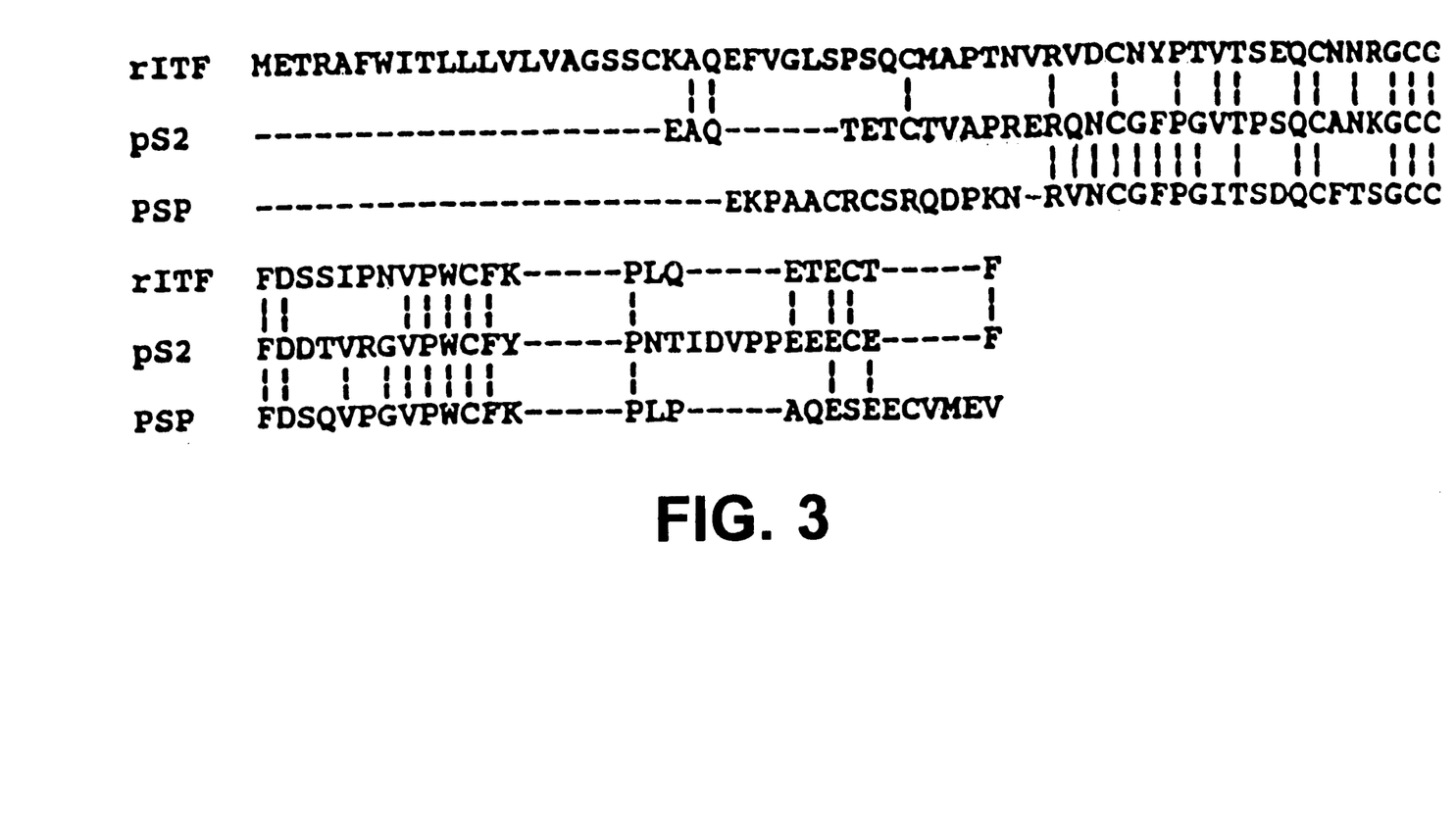
FIG. 3 is a depiction of the amino acid sequences of rat intestinal trefoil factor, pS2 protein, and pancreatic spasmolytic polypeptide. The sequences are aligned so as to illustrate the amino acid sequence homology between the proteins. Dashes (—) indicate the insertion of spaces which improve alignment. Bars (|) indicate sequence identities.
Figure 4A:
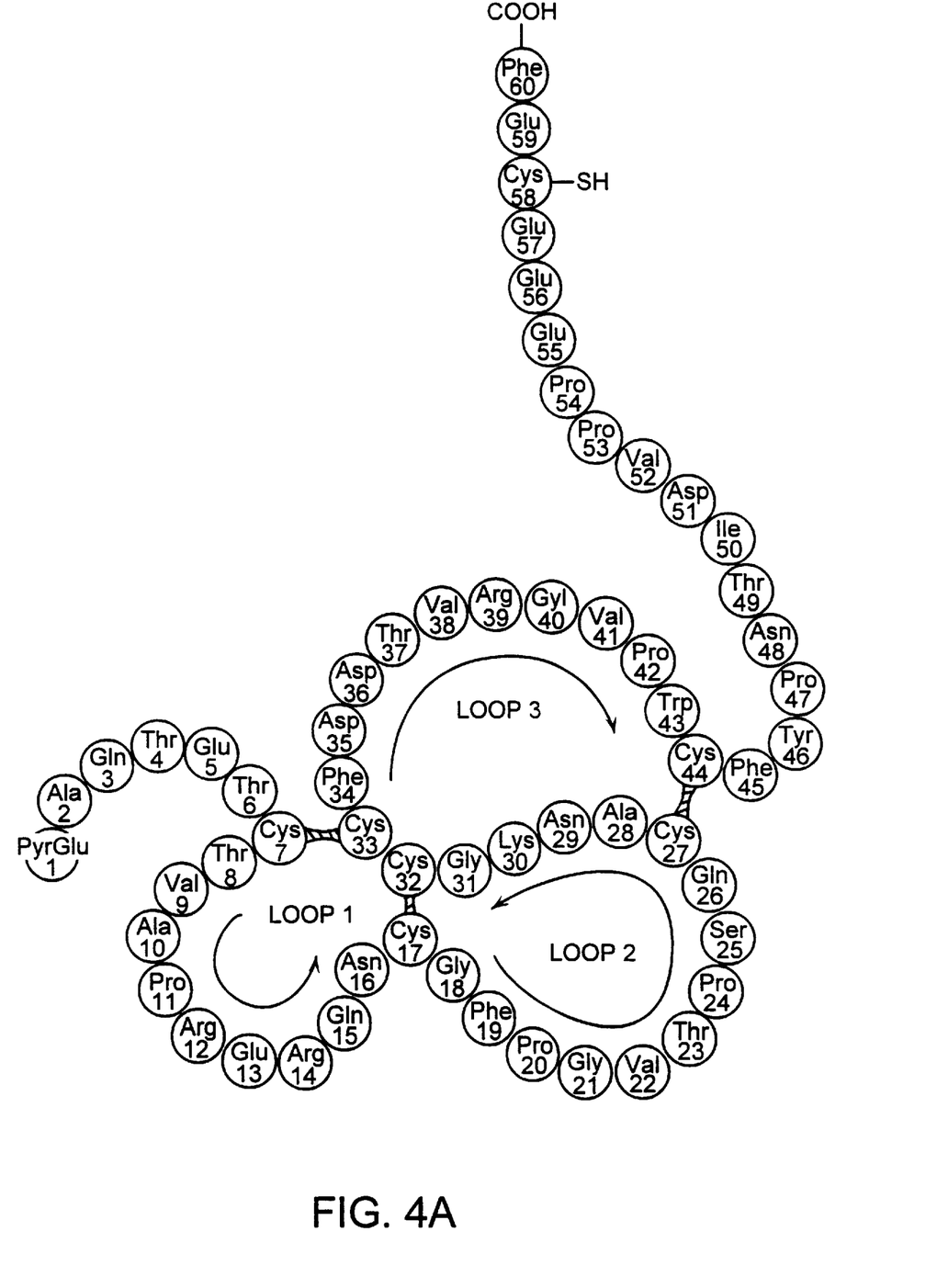
FIG. 4 depicts the disulfide bond structure proposed for pS2 (panel A SEQ ID NO: 4) and PSP (panel B; SEQ ID NO: 6)
Figure 4B:
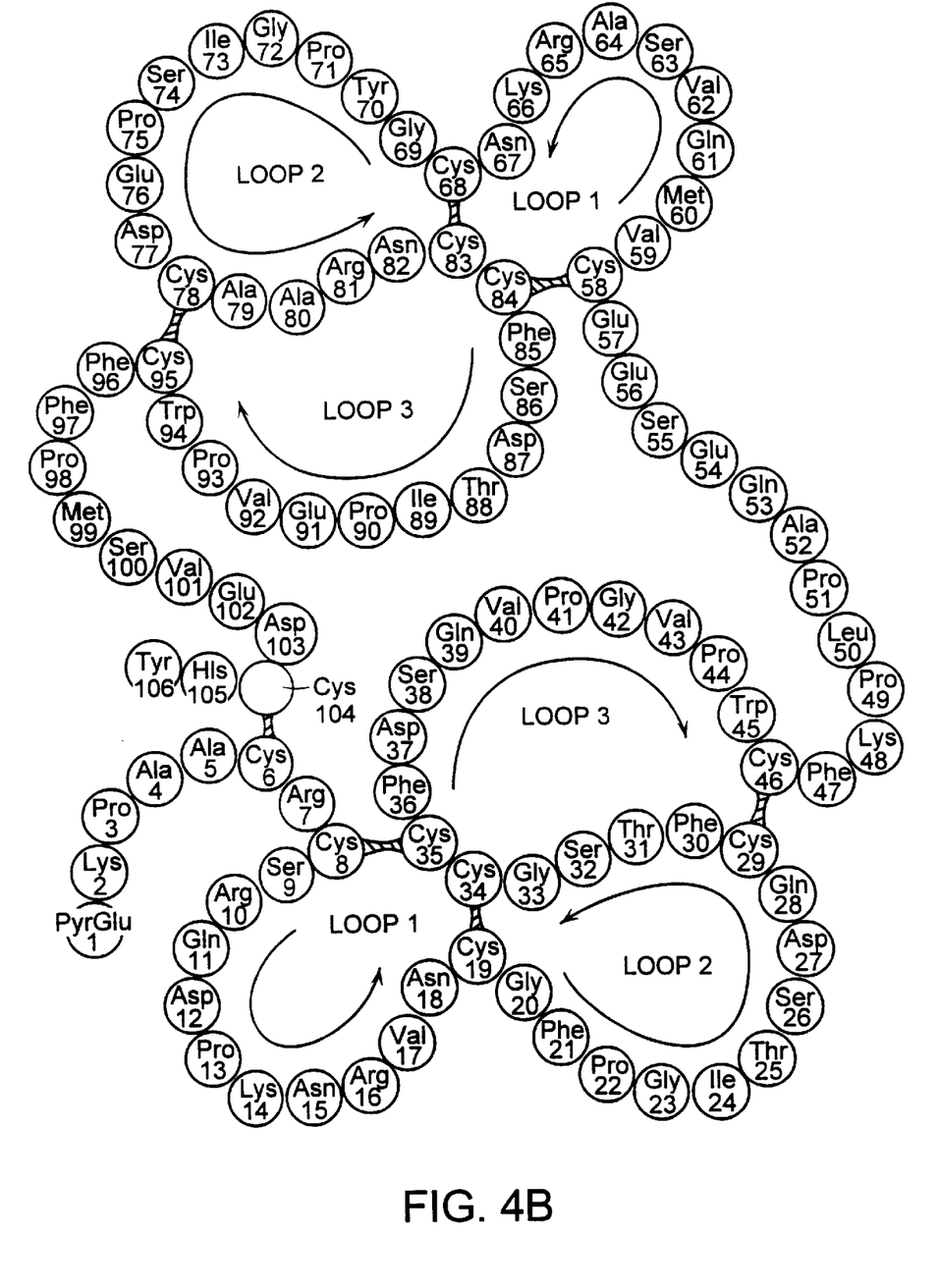
Figure 5:
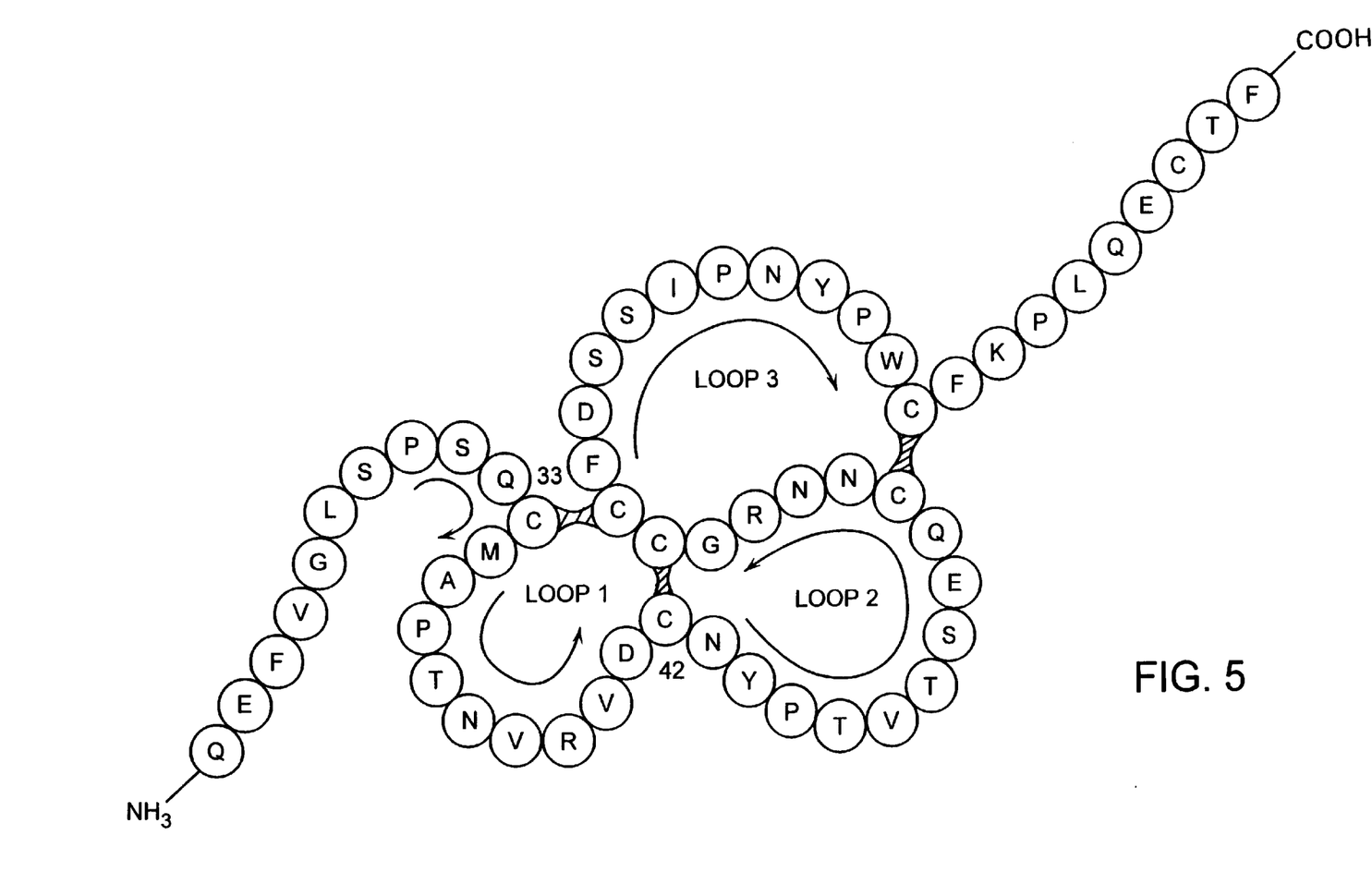
FIG. 5 is a depiction of the proposed disulfide bond structure of rat intestinal trefoil factor (SEQ ID NO: 7).

The open reading frame of clone T3411 encoded an 81 amino acid peptide (FIG. 2; SEQ ID NO 2). Comparison of the sequence of the encoded peptide, referred to as rat intestinal trefoil factor (rITF), to the sequence of proteins in the Genebank database revealed significant homology to human breast cancer associated peptide (pS2; Jakowlev et al., *Nucleic Acids Res.* 12:2861, 1984) and porcine pancreatic spasmolytic peptide (PSP; Thim et al., *Biochem. Biophys. Acta* 827:410, 1985). FIG. 3 illustrates the homology between rITF, PSP and pS2. Porcine pancreatic spasmolytic factor (PSP) and pS2 are both thought to fold into a characteristic structure referred to as a trefoil. A trefoil structure consists of three loops formed by three disulfide bonds. pS2 is thought to include one trefoil (FIG. 4A), and PSP is thought to include two trefoils (FIG. 4B). The region of rITF (nucleotide 114 to nucleotide 230 which encodes cys to phe) which is most similar to PSP and pS2 includes six cysteines all of which are in the same position as the cysteines which make up the trefoil in pS2 (FIG. 3). Five of these six cysteines are in the same position as the cysteines which form the amino terminal trefoil of PSP (FIG. 3). FIG. 5 depicts the proposed disulfide bond configuration of rITF.

Based on homology to PSP and pS2 (Mori et al., *Biochem. Biophys. Res. Comm.* 155:366, 1988; Jakowlew et al., *Nucleic Acids Res.* 12:2861, 1984), rITF includes a presumptive pro- sequence (met$^1$ to ala$^{22}$) in which 12 of 22 amino acids have hydrophobic side chains.

Production of Anti-rITF Antibodies

A peptide corresponding to the carboxy-terminal 21 amino acids of rITF was synthesized and coupled to bovine serum albumin (BSA). This conjugate (and the unconjugated peptide) was used to raise polyclonal antibodies in rabbits. All procedures were standard protocols such as those described in Ausubel et al. (supra). The anti-rITF antibodies were used in an indirect immunoflouresce assay for visualization of rITF in rat tissues. Cryosections of rat tissues were prepared using standard techniques, and fluorescein labelled goat anti-rabbit monoclonal antibody (labelled antibodies are available from such suppliers Kirkegaard and Perry Laboratories, Gaithersberg, Md.; and Bioproducts for Science, Inc., Indianapolis, Ind.) was used to detect binding of rabbit anti-rITF antibodies. By this analysis rITF appears to be present in the globlet cells of the small intestine but not in the stomach or the pancreas.

Cloning of Human Intestinal Trefoil Factor

DNA encoding the rat intestinal trefoil factor can be used to identify a cDNA clone encoding the human intestinal trefoil factor (hITF). This can be accomplished by screening a human colon cDNA library with a probe derived from rITF or with a probe derived from part of the hITF gene. The latter probe can be obtained from a human colon or intestinal cDNA using the polymerase chain reaction to isolate a part of the hITF gene. This probe can then serve as a specific probe for the identification of clones encoding all of the hITF gene.

Construction of a cDNA Library.

A human colon or intestinal cDNA library in λgtlO or λgtll, or some other suitable vector is useful for isolation of hITF. Such libraries may be purchased (Clontech Laboratories, Palo Alto, Calif.: HLI034a, HLI0346b). Alternatively, a library can be produced using mucosal scrapings from human colon or intestine. Briefly, total RNA is isolated from the tissue essentially as described by Chirgwin et al. (*Biochemistry* 18:5294, 1979; see also Ausubel et al., supra). An oligo (dT) column is then used to isolate poly(A)$^+$ RNA by the method of Aviv et al. (*J. Mol. Biol.* 134:743, 1972; see also Ausubel et al., supra). Double-stranded cDNA is then produced by reverse transcription using oligo (dT)$_{12-18}$ or random hexamer primers (or both). RNAse H and *E. coli* DNA polI are then used to replace the RNA strand with a second DNA strand. In a subsequent step *E. coli* DNA ligase and T4 DNA polymerase are used to close gaps in the second DNA strand and create blunt ends. Generally, the cDNA created is next methylated with EcoRI methylase and EcoRI linkers are added (other linkers can be used depending on the vector to be used). In subsequent steps the excess linkers are removed by restriction digestion and the cDNA fragments are inserted into the desired vector. See Ausubel et al., supra and Sambrook et al. (*Molecular Cloning: A Laboratory Manual*, Cold Spring Harbor Laboratory, Cold Spring Harbor, N.Y., 1990) for detailed protocols. Useful vectors include: λgtll, λgtlO, Lambda ZAP® II vector, Lambda Uni-ZAP™ XR vector, all available from Stratagene (La Jolla, Calif.).

The cDNA library must be packaged into phage; this is most readily accomplished by use of a commercial in vitro packaging kit, e.g., Gigapack® II Gold or Gigapack® II Plus (Stratagene, La Jolla, Calif.). See Ausubel et al. (supra) for packaging protocols and suitable host strains. The library is preferably amplified soon after packaging; this step generates sufficient clones for multiple screening of the library. See Ausubel et al. supra or Sambrook et al. supra for details of amplification protocols and procedures for storing the amplified library.

Screening of the cDNA Library

To screen the library it must be placed on an appropriate host strain (e.g., Y1090 or Y1088 for λgtlO libraries, C600hflA for λgtlO libraries). After plating the phage, plaques are transferred to nitrocellulose or nylon filters (See Ausubel et al., supra and Sambrook et al. supra). The filters are then probed with α$^{32}$P-labelled nick translated probe derived from rITF. The probe is preferentially generated using a portion of the region of rITF DNA coding for the trefoil structure (nucleotides 114 to 230 of SEQ ID NO. 1 which encode cys$^{33}$ to phe$^{71}$ of SEQ ID NO. 2). This region is conserved between rITF, pS2 and PSP, and it is likely that this region is conserved between rITF and hITF. Once a plaque is identified several cycles of plaque purification are required to isolate a pure clone encoding hITF. A phage DNA isolation is performed and the cDNA insert can be subcloned into an appropriate vector for restriction mapping and sequencing. If the phage vector is Lambda ZAP® II, coinfection with helper phage allows rescue and recircularization of pBluescript SK$^-$ phagemid vector (Stratagene, La Jolla, Calif.) harboring the cDNA; alternatively the phage clone is purified and the cDNA insert is subcloned into a vector suitable for restriction mapping and sequencing. If the clone does not contain the entire hITF gene (as assessed by homology to rITF and the presence of start and stop codons), the library can be rescreened with the original rITF probe or, preferably, with a probe generated from the hITF clone obtained. If none of the clones contain the intact gene, it can be reconstructed from clones which bear overlapping fragments of hITF.

Direct Isolation of an hITF Probe by PCR

It is possible to isolate part of the hITF gene directly from the packaged library or cDNA. To isolate a portion of hITF directly from the packaged library, a pair of oligonucleotide primers and Taq polymerase are used to amplify the DNA corresponding to the hITF gene. The primers used would be approximately 15–20 nucleotides long and correspond in sequence to the 5'-most and 3'-most portions of the rITF coding sequence. Friedman et al. (in PCR *Protocols: A Guide to Methods and Applications,* Innis et al., eds., Academic Press, San Diego) describe a procedure for such amplification. Briefly, phage particles are disrupted by heating; Taq polymerase, primers (300 pmol of each), dNTPs, and Taq polymerase buffer are added; and the mixture is thermally cycled to amplify DNA. The amplified DNA is isolated by agarose gel electrophoresis. The ends of the fragment are prepared for ligation into an appropriate vector by making them flush with T4 polymerase and, if desired, adding linkers. Alternatively, a restriction site may be engineered into the fragment by using primers which have sequence added to their 5' ends which sequence will generate an appropriate sticky end when digested. For example the sequence: 5=-GGGCGGCCGC-3' (SEQ ID NO: 8) can be added to the 5' end of each primer. This sequence includes the NotI restriction site flanked at the 5' end by the sequence: GG. The additional nucleotides prevent the 5' ends from denaturing and interfering with subsequent restriction digestion with NotI. The gel purified DNA of the appropriate size is next cloned into a cloning vector for sequencing and restriction mapping. This clone will not have the entire hITF sequence, rather it will be a combination of hITF (the region between the sequences corresponding to the primers) and rITF (the 5' and 3' ends which correspond to the primer sequences). However, this DNA can be used to generate a labelled probe (produced by nick translation or random primer labelling) which, since it is the correct hITF sequence, can be used in a high stringency screening of the library from which the cDNA was originally isolated. In an alternative approach, cDNA can be used in the above procedure instead of a packaged library. This eliminates the steps of modifying the cDNA for insertion into a vector as well as cDNA packaging and library amplification. Ausubel et al. supra provides a protocol for amplification of a particular DNA fragment directly from cDNA and a protocol for amplification from poly(A)$^+$ RNA.

Identification of a Presumptive Human ITF Clone

A nick translated probe derived from rITF cDNA (corresponding to nucleotides 1 to 431 of SEQ ID No. 1) was used for Northern blot analysis of poly(A)$^+$ RNA derived from human intestinal mucosal scrapings. Probe hybridization and blot washing were carried out according to standard procedures. Probe ($5 \times 10^5$ cpm/ml hybridization buffer) was hybridized to the filter at 45° C. in 5X SSC with 30% formamide. The filter was then washed at 60° C. in 5X SSC with 40% formamide. Using this protocol a band was clearly visible after an overnight exposure of the filter with an intensifying screen. This result indicated that there is sufficient homology between rITF and hITF to allow the use of probes derived from the sequence of the rITF gene for identification of the hITF gene.

A human intestinal cDNA library was obtained from Clontech (Palo Alto, Calif.). Alternatively, a human intestinal cDNA library may be produced from mucosal scrapings as described above. Four oligonucleotide probes were selected for screening the library cDNA. Two of the probes correspond to sequences within the region of rITF encoding the trefoil and are referred to as internal probes (5'-gtacattctgtctcttgcaga-3' (SEQ ID NO: 9) and 5'-taaccctgctgctgctggtcctgg-3' (SEQ ID NO: 10)). The other two probes recognize sequences within rITF but outside of the trefoil encoding region and are referred to as external probes (5'-gtttgcgtgctgccatggaga-3' (SEQ ID NO: 11) and 5'-ccgcaattagaacagccttgt-3' (SEQ ID NO: 12)). These probes were tested for their utility by using them to screen the rat intestinal cDNA library described above. Each of the four probes could be used to identify a clone harboring all or part of the rITF gene. This result indicates that these probes may be used to screen the human intestinal library for the presence of hITF.

The internal probes were used as described above to amplify a DNA fragment from human colon library cDNA (Clontech, Palo Alto, Calif.). Linkers were added to the isolated DNA fragment which was then inserted into pBluescript phagemid vector (Stratagene, La Jolla, Calif.). The region of this clone corresponding to the sequence of human cDNA (i.e., not including the sequence corresponding to the internal probes) was used to make a radioactively labelled probe by random oligonucleotide-primed synthesis (Ausubel et al., supra). This probe was then used to screen the human colon cDNA library. This screening led to the identification of 29 clones. One of these clones (HuPCR—ITF) was nick-translated to generate a probe for Northern analysis of poly(A)$^+$ RNA isolated from human intestinal mucosal scrapings. A single band of roughly the same size as the rat transcript (approximately 0.45 kDa) was observed.

Northern analysis of poly(A)$^+$ isolated from human tissues indicated that RNA corresponding to this probe was expressed in the small intestine and the large intestine but not in the stomach or the liver. These results indicate that the clone does not encode the human homolog of porcine PSP. Porcine PSP is expressed in porcine pancreas and is not significantly expressed in the small or large intestine. These results also distinguish the cloned gene from pS2 which is expressed in the stomach.

Figure 6:
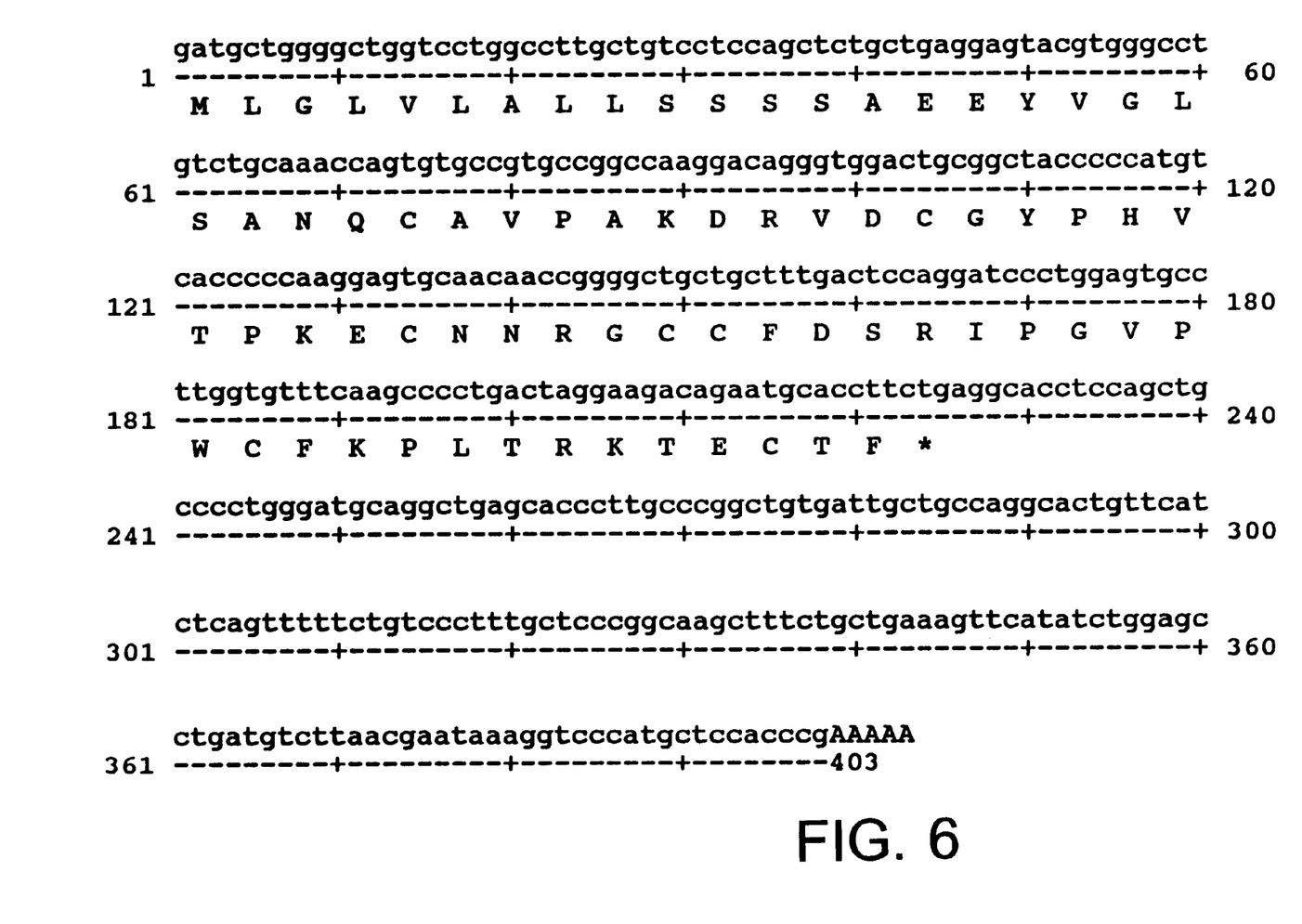
FIG. 6 is a depiction of the nucleotide sequence of the human intestinal trefoil factor cDNA and the corresponding deduced amino acid sequence (SEQ ID NO: 3).

FIG. 6 shows the nucleic acid sequence information for human ITF cDNA, along with the deduced amino acid sequence in one-letter code (SEQ ID NO: 3). This clone was obtained by the methods described above.

Production of hITF

The isolated hITF gene can be cloned into a mammalian expression vector for protein expression. Appropriate vectors include pMAMneo (Clontech, Palo Alto, Calif.) which provides a RSV-LTR enhancer linked to a dexamethasone-inducible MMTV-LTR promoter, an SV40 origin of replication (allows replication in COS cells), a neomycin gene, and SV40 splicing and polyadenylation sites. This vector can be used to express the protein in COS cells, CHO cells, or mouse fibroblasts. The gene may also be cloned into a vector for expression in Drosophila cells using the baculovirus expression system.

Purification of Intestinal Trefoil Factor

Intestinal trefoil factor can be purified from intestinal mucosal scrapings of human, rats or any other species which expresses ITF (pigs and cows may provide a source of ITF). The purification procedure used for PSP will be useful for the purification of ITF since the proteins are likely to be homologous. Jorgensen et al. describes a method for purification of PSP (Regulatory Peptides 3:207, 1982). The preferred method is the second approach described by Jorgensen et al. (supra). This method involves chromatography of SP-Sephadex C-25 and QAE Sephadex A-25 columns (Sigma, St. Louis, Mo.) in acidic buffer. *Anti-Intestinal Trefoil Factor Monoclonal Antibodies*

Anti-intestinal trefoil factor monoclonal antibodies can be raised against synthetic peptides whose sequences are based on the deduced amino acid sequence of cloned hITF (SEQ ID NO: 4). Most commonly the peptide is based on the amino- or carboxy-terminal 10–20 amino acids of the protein of interest (here hITF). The peptide is usually chemically cross-linked to a carrier molecule such as bovine serum albumin or keyhole limpet hemocyanin. The peptide is selected with the goal of generating antibodies which will cross-react with the native hITF. Accordingly, the peptide should correspond to an antigenic region of the peptide of interest. This is accomplished by choosing a region of the protein which is (1) surface exposed, e.g., a hydrophobic region or (2) relatively flexible, e.g., a loop region or a β-turn region. In any case, if the peptide is to be coupled to a carrier it must have an amino acid with a side chain capable of participating in the coupling reaction. See Hopp et al. (*Mol. Immunol.* 20:483, 1983; *J. Mol. Biol.* 157:105, 1982) for a discussion of the issues involved in the selection of antigenic peptides. A second consideration is the presence of a protein homologous to hITF in the animal to be immunized. If such a protein exists, it is important to select a region of hITF which is not highly homologous to that homolog.

For hITF, peptides that correspond to the amino-terminal or carboxy-terminal 15 amino acids are likely to be less homologous across species and exposed to the surface (and thus antigenic). Thus they are preferred for the production of monoclonal antibodies. Purified hITF can also be used for the generation of antibodies.

Use

In the practice of the present invention ITF may be administered orally, intravenously, or intraperitoneally for treatment of peptic ulcer diseases, inflammatory bowel diseases, and for protection of the intestinal tract from injury caused by bacterial infection, radiation injury or other insults. The mode of administration, dosage, and formulation of ITF depends upon the condition being treated.

Deposit Statement

The human intestinal trefoil clone described herein has been deposited under conditions in which access will be available during the pendency of the present patent application to those determined by the Commissioner of Patents and Trademarks to be entitled thereto under 37 C.F.R. § 1.14 and 35 U.S.C. § 122. More specifically, the human intestinal trefoil clone described herein has been deposited with the American Type Culture Collection (Manassas, Va.) and assigned Accession Number 98767.

The address of the American Type Culture Collection is 10801 University Boulevard, Manassas, Va. 20110-2209.

Other Embodiments

Other embodiments are within the following claims. For example, ITF may be used to produce monoclonal antibodies for the detection of ITF in intestinal tissue or blood serum by means of an indirect immunoassay. ITF may be detectably labelled and used in an in situ hybridization assay for the detection of ITF binding sites. Labels may include, but are not limited to, florescein or a radioactive ligand.

ITF may be used to protect and stabilize other proteins. This protection is accomplished by forming a hybrid molecule in which all or part of ITF is fused to either the carboxy-terminus or the amino-terminus (or both) of the protein of interest. Because ITF is resistant to degradation in the digestive system, it will protect the protein of interest from such degradation. As a consequence, the protein of interest is likely to remain active in the digestive system and/or will be more readily absorbed in an intact form.

What is claimed is:

1. A substantially pure polypeptide comprising an amino acid sequence encoded by the cDNA clone deposited with the American Type Culture Collection and assigned Accession Number 98767.

2. The polypeptide of claim 1, wherein the polypeptide is detectably labelled.

3. A therapeutic composition comprising the polypeptide of claim 1 and a pharmacologically acceptable carrier.

4. A method for treating digestive disorders in a human patient, comprising administering to the patient the therapeutic composition of claim 3.

5. A method for detecting binding sites for intestinal trefoil factor in a patient, the method comprising contacting a biological sample obtained from the patient with the polypeptide of claim 1, and detecting the polypeptide bound to the biological sample as an indication of the presence of the binding sites in the sample.

6. A substantially pure polypeptide, the polypeptide comprising SEQ ID NO: 2.

7. A method for treating digestive disorders in a human patient, the method comprising administering to the patient a therapeutic composition comprising rat ITF (SEQ ID NO: 2).

8. A method for detecting binding sites for intestinal trefoil factor in a patient, the method comprising contacting a biological sample obtained from the patient with a polypeptide comprising SEQ ID NO: 2 and detecting the polypeptide bound to the biological sample as an indication of the presence of the binding sites in the sample.

* * * * *

UNITED STATES PATENT AND TRADEMARK OFFICE
CERTIFICATE OF CORRECTION

PATENT NO. : 6,063,755 Page 1 of 1
DATED : May 16, 2000
INVENTOR(S) : Daniel K. Podolsky It is certified that error appears in the above-identified patent and that said Letters Patent is hereby corrected as shown below:

<u>Column 7,</u>
Line 18, "5=–GGGCGGCCGC–3'" should be -- 5'–GGGCGGCCGC–3' --

<u>Column 9,</u>
Line 14, "a carrier it" should be -- a carrier, it --

<u>Column 17,</u>
Line 21, "to the patient" should be -- to said patient --
Line 25, "from the patient" should be -- from said patient --

<u>Column 18,</u>
Line 11, "the biological" should be -- said biological --
Line 12, "the binding" should be -- said binding --
Line 13, "the sample" should be -- said sample --
Line 14, "the polypeptide" should be -- said polypeptide --

Signed and Sealed this

Twenty-fourth Day of December, 2002

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 431 base pairs
      (B) TYPE: nucleic acid
      (C) STRANDEDNESS: single
      (D) TOPOLOGY: linear    (xi) SEQUENCE DESCRIPTION: SEQ ID NO:1:

```
GAAGTTTGCG TGCTGCC ATG GAG ACC AGA GCC TTC TGG ATA ACC CTG CTG          50
                Met Glu Thr Arg Ala Phe Trp Ile Thr Leu Leu
                 1               5                  10

CTG GTC CTG GTT GCT GGG TCC TCC TGC AAA GCC CAG GAA TTT GTT GGC          98
Leu Val Leu Val Ala Gly Ser Ser Cys Lys Ala Gln Glu Phe Val Gly
            15                  20                  25

CTA TCT CCA AGC CAA TGT ATG GCG CCA ACA AAT GTC AGG GTG GAC TGT         146
Leu Ser Pro Ser Gln Cys Met Ala Pro Thr Asn Val Arg Val Asp Cys
        30                  35                  40

AAC TAC CCC ACT GTC ACA TCA GAG CAG TGT AAC AAC CGT GGT TGC TGT         194
Asn Tyr Pro Thr Val Thr Ser Glu Gln Cys Asn Asn Arg Gly Cys Cys
    45                  50                  55

TTT GAC TCC AGC ATC CCA AAT GTG CCC TGG TGC TTC AAA CCT CTG CAA         242
```

```
Phe Asp Ser Ser Ile Pro Asn Val Pro Trp Cys Phe Lys Pro Leu Gln
 60                  65                  70                  75

GAG ACA GAA TGT ACA TTT TGAAGCTGTC CAGGCTCCAG GAAGGGAGCT CCACACCC      298
Glu Thr Glu Cys Thr Phe
                 80

TGGACTCTTG CTGATGGTAG TGGCCCAGGG TAACACTCAC CCCTGATCTG CTCCCTCGCG      358

CCGGCCAATA TAGGAGCTGG GAGTCCAGAA GAATAAAGAC CTTACAGTCA GCACAAGGCT      418

GTTCTAATTG CGG                                                         431

(2) INFORMATION FOR SEQ ID NO:2:

(i) SEQUENCE CHARACTERISTICS:
         (A) LENGTH: 81 amino acids
         (B) TYPE: amino acid
         (D) TOPOLOGY: linear (xi) SEQUENCE DESCRIPTION: SEQ ID NO:2:

Met Glu Thr Arg Ala Phe Trp Ile Thr Leu Leu Val Leu Val Ala
 1               5                  10                  15

Gly Ser Ser Cys Lys Ala Gln Glu Phe Val Gly Leu Ser Pro Ser Gln
                20                  25                  30

Cys Met Ala Pro Thr Asn Val Arg Val Asp Cys Asn Tyr Pro Thr Val
                35                  40                  45

Thr Ser Glu Gln Cys Asn Asn Arg Gly Cys Cys Phe Asp Ser Ser Ile
            50                  55                  60

Pro Asn Val Pro Trp Cys Phe Lys Pro Leu Gln Glu Thr Glu Cys Thr
 65                 70                  75                  80

Phe (2) INFORMATION FOR SEQ ID NO:3:

(i) SEQUENCE CHARACTERISTICS:
         (A) LENGTH: 403 base pairs
         (B) TYPE: nucleic acid
         (C) STRANDEDNESS: single
         (D) TOPOLOGY: linear (xi) SEQUENCE DESCRIPTION: SEQ ID NO:3:

G ATG CTG GGG CTG GTC CTG GCC TTG CTG TCC TCC AGC TCT GCT GAG GAG       49
  Met Leu Gly Leu Val Leu Ala Leu Leu Ser Ser Ser Ala Glu Glu
   1               5                  10                  15

TAC GTG GGC CTG TCT GCA AAC CAG TGT GCC GTG CCG GCC AAG GAC AGG         97
Tyr Val Gly Leu Ser Ala Asn Gln Cys Ala Val Pro Ala Lys Asp Arg
                20                  25                  30

GTG GAC TGC GGC TAC CCC CAT GTC ACC CCC AAG GAG TGC AAC AAC CGG        145
Val Asp Cys Gly Tyr Pro His Val Thr Pro Lys Glu Cys Asn Asn Arg
            35                  40                  45

GGC TGC TGC TTT GAC TCC AGG ATC CCT GGA GTG CCT TGG TGT TTC AAG        193
Gly Cys Cys Phe Asp Ser Arg Ile Pro Gly Val Pro Trp Cys Phe Lys
        50                  55                  60

CCC CTG ACT AGG AAG ACA GAA TGC ACC TTC TGAGGCACCT CCAGCTGCCC CTG      246
Pro Leu Thr Arg Lys Thr Glu Cys Thr Phe
 65                 70

GGATGCAGGC TGAGCACCCT TGCCCGGCTG TGATTGCTGC CAGGCACTGT  TCATCTCAGT    306

TTTTCTGTCC CTTTGCTCCC GGCAAGCTTT CTGCTGAAAG TTCATATCTG  GAGCCTGATG    366

TCTTAACGAA TAAAGGTCCC ATGCTCCACC CGAAAAA                              403

(2) INFORMATION FOR SEQ ID NO:4:
```

(i) SEQUENCE CHARACTERISTICS:
    (A) LENGTH: 74 amino acids
    (B) TYPE: amino acid
    (D) TOPOLOGY: linear (xi) SEQUENCE DESCRIPTION: SEQ ID NO:4:

Met Leu Gly Leu Val Leu Ala Leu Leu Ser Ser Ser Ser Ala Glu Glu
 1               5                  10                  15

Tyr Val Gly Leu Ser Ala Asn Gln Cys Ala Val Pro Ala Lys Asp Arg
                 20                  25                  30

Val Asp Cys Gly Tyr Pro His Val Thr Pro Lys Glu Cys Asn Asn Arg
             35                  40                  45

Gly Cys Cys Phe Asp Ser Arg Ile Pro Gly Val Pro Trp Cys Phe Lys
 50                  55                  60

Pro Leu Thr Arg Lys Thr Glu Cys Thr Phe
 65                  70

(2) INFORMATION FOR SEQ ID NO:5:

(i) SEQUENCE CHARACTERISTICS:
        (A) LENGTH: 60 amino acids
        (B) TYPE: amino acid
        (D) TOPOLOGY: linear (xi) SEQUENCE DESCRIPTION: SEQ ID NO:5:

Glu Ala Gln Thr Glu Thr Cys Thr Val Ala Pro Arg Glu Arg Gln Asn
 1               5                  10                  15

Cys Gly Phe Pro Gly Val Thr Pro Ser Gln Cys Ala Asn Lys Gly Cys
                 20                  25                  30

Cys Phe Asp Asp Thr Val Arg Gly Val Pro Trp Cys Phe Tyr Pro Asn
             35                  40                  45

Thr Ile Asp Val Pro Pro Glu Glu Glu Cys Glu Phe
 50                  55                  60

(2) INFORMATION FOR SEQ ID NO:6:

(i) SEQUENCE CHARACTERISTICS:
        (A) LENGTH: 62 amino acids
        (B) TYPE: amino acid
        (D) TOPOLOGY: linear (xi) SEQUENCE DESCRIPTION: SEQ ID NO:6:

Glu Lys Pro Ala Ala Cys Arg Cys Ser Arg Gln Asp Pro Lys Asn Arg
 1               5                  10                  15

Val Asn Cys Gly Phe Pro Gly Ile Thr Ser Asp Gln Cys Phe Thr Ser
                 20                  25                  30

Gly Cys Cys Phe Asp Ser Gln Val Pro Gly Val Pro Trp Cys Phe Lys
             35                  40                  45

Pro Leu Pro Ala Gln Glu Ser Glu Glu Cys Val Met Glu Val
 50                  55                  60

(2) INFORMATION FOR SEQ ID NO:7:

(i) SEQUENCE CHARACTERISTICS:
        (A) LENGTH: 106 amino acids
        (B) TYPE: amino acid
        (D) TOPOLOGY: linear (xi) SEQUENCE DESCRIPTION: SEQ ID NO:7:

Glu Lys Pro Ala Ala Cys Arg Cys Ser Arg Gln Asp Pro Lys Asn Arg
 1               5                  10                  15

```
Val Asn Cys Gly Phe Pro Gly Ile Thr Ser Asp Gln Cys Phe Thr Ser
         20                  25                  30

Gly Cys Cys Phe Asp Ser Gln Val Pro Gly Val Pro Trp Cys Phe Lys
         35                  40                  45

Pro Leu Pro Ala Gln Glu Ser Glu Glu Cys Val Met Glu Val Ser Ala
         50                  55                  60

Arg Lys Asn Cys Gly Tyr Pro Gly Ile Ser Pro Glu Asp Cys Ala Ala
 65                  70                  75                  80

Arg Asn Cys Cys Phe Ser Asp Thr Ile Pro Glu Val Pro Trp Cys Phe
             85                   90                  95

Phe Pro Met Ser Val Glu Asp Cys His Tyr
            100                 105
```

(2) INFORMATION FOR SEQ ID NO:8:

(i) SEQUENCE CHARACTERISTICS:
    (A) LENGTH: 10 base pairs
    (B) TYPE: nucleic acid
    (C) STRANDEDNESS: single
    (D) TOPOLOGY: linear   (xi) SEQUENCE DESCRIPTION: SEQ ID NO:8:

GGGCGGCCGC                  10

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear   (xi) SEQUENCE DESCRIPTION: SEQ ID NO:9:

GTACATTCTG TCTCTTGCAG A            21

(2) INFORMATION FOR SEQ ID NO:10:

(i) SEQUENCE CHARACTERISTICS:
    (A) LENGTH: 24 base pairs
    (B) TYPE: nucleic acid
    (C) STRANDEDNESS: single
    (D) TOPOLOGY: linear   (xi) SEQUENCE DESCRIPTION: SEQ ID NO:10:

TAACCCTGCT GCTGCTGGTC CTGG          24

(2) INFORMATION FOR SEQ ID NO:11:

(i) SEQUENCE CHARACTERISTICS:
    (A) LENGTH: 21 base pairs
    (B) TYPE: nucleic acid
    (C) STRANDEDNESS: single
    (D) TOPOLOGY: linear   (xi) SEQUENCE DESCRIPTION: SEQ ID NO:11:

GTTTGCGTGC TGCCATGGAG A           21

(2) INFORMATION FOR SEQ ID NO:12:

(i) SEQUENCE CHARACTERISTICS:
    (A) LENGTH: 21 base pairs
    (B) TYPE: nucleic acid -continued

```
        (C) STRANDEDNESS: single
        (D) TOPOLOGY: linear (xi) SEQUENCE DESCRIPTION: SEQ ID NO:12:

CCGCAATTAG AACAGCCTTG T                                          21
```